United States Patent
Wahl et al.

(10) Patent No.: US 11,376,137 B2
(45) Date of Patent: Jul. 5, 2022

(54) POWERED GEARBOX FOR PROSTHETIC ELBOW JOINT

(71) Applicant: Hugh Steeper Limited, Leeds (GB)

(72) Inventors: Ryan Wahl, Richmond, MI (US); Aaron Taszreak, China, MI (US)

(73) Assignee: Hugh Steeper Limited, Leeds (GB)

(*) Notice: Subject to any disclaimer, the term of this patent is extended or adjusted under 35 U.S.C. 154(b) by 202 days.

(21) Appl. No.: 16/791,332

(22) Filed: Feb. 14, 2020

(65) Prior Publication Data
US 2021/0251778 A1    Aug. 19, 2021

(51) Int. Cl.
| | |
|---|---|
| *A61F 2/58* | (2006.01) |
| *F16H 13/08* | (2006.01) |
| *F16H 37/02* | (2006.01) |
| *F16H 49/00* | (2006.01) |
| *F16H 57/02* | (2012.01) |
| *A61F 2/54* | (2006.01) |
| *A61F 2/68* | (2006.01) |

(52) U.S. Cl.
CPC .............. *A61F 2/582* (2013.01); *F16H 13/08* (2013.01); *F16H 37/02* (2013.01); *F16H 49/001* (2013.01); *F16H 57/02* (2013.01); *A61F 2002/543* (2013.01); *A61F 2002/6836* (2013.01); *F16H 2057/02039* (2013.01); *F16H 2702/02* (2013.01)

(58) Field of Classification Search
CPC .... A61F 2/58; A61F 2/582; A61F 2002/5039; A61F 2002/543; A61F 2002/6836; F16H 13/08; F16H 37/02; F16H 49/001; F16H 57/02; F16H 2057/02039; F16H 2702/02
See application file for complete search history.

(56) References Cited

U.S. PATENT DOCUMENTS

| | | | |
|---|---|---|---|
| 3,883,990 A | 5/1975 | Stidolph | |
| 8,197,554 B2* | 6/2012 | Whiteley | H02K 7/116 623/24 |
| 9,839,534 B2 | 12/2017 | Lipsey et al. | |
| 10,113,618 B2 | 10/2018 | Schorsch | |
| 10,369,016 B2* | 8/2019 | Lipsey | H02K 7/116 |
| 10,919,161 B2* | 2/2021 | Smith | B25J 17/0241 |
| 2016/0053858 A1* | 2/2016 | Brassitos | H02K 21/22 475/331 |
| 2018/0168830 A1* | 6/2018 | Evans | A61F 2/585 |

(Continued)

*Primary Examiner* — Bruce E Snow
(74) *Attorney, Agent, or Firm* — Rahman LLC

(57) ABSTRACT

A prosthetic elbow includes a fixed member structure and a powered gearbox mechanism housed in a housing structure for rotating the forearm portion to varying angular positions. The powered gearbox mechanism includes a motor attached to the housing structure, a planetary frictional drive connected to a motor shaft of the motor and the housing structure, and a strain wave gear set having an input driven by the planetary fictional drive and an output attached to the fixed member structure, where the powered gearbox mechanism is configured to convert an output of the motor into a rotation of the housing structure relative to the fixed member structure, thereby causing the rotation of the forearm portion to varying angular positions relative to the upper arm. The fixed member structure and the housing structure each are connected to one of a forearm portion and an upper arm portion and rotatable relative to one another about an axis of rotation of the forearm portion.

7 Claims, 10 Drawing Sheets

(56) References Cited

U.S. PATENT DOCUMENTS

| | | | |
|---|---|---|---|
| 2018/0209529 A1 | 7/2018 | Frey et al. | |
| 2019/0263007 A1* | 8/2019 | Cui | B25J 18/04 |
| 2020/0352811 A1* | 11/2020 | Varghese | B25J 9/102 |
| 2021/0023699 A1* | 1/2021 | Darby | B25J 13/088 |
| 2021/0251778 A1* | 8/2021 | Wahl | F16H 37/02 |

* cited by examiner

POWERED GEARBOX FOR PROSTHETIC ELBOW JOINT

FIELD OF THE INVENTION

The invention relates to a prosthetic elbow with a gearbox mechanism to rotate the mass of terminal devices such as arms and hands to varying angular positions.

BACKGROUND OF THE INVENTION

Prosthetic elbows typically include a forearm and a fixed member structure that is configured to connect to an upper arm portion. The forearm member may be flexed either directly or by mechanical connection via a harness to the person's body. An end effector is typically added to the end of the forearm to grasp objects. A powered gearbox mechanism may be incorporated into the prosthetic elbow to rotate the forearm and end effector.

SUMMARY OF THE INVENTION

The embodiments of the present invention provides a prosthetic elbow with a powered gearbox mechanism for rotating the forearm portion to varying angular positions about an elbow axis. The prosthetic elbow may include a fixed member structure configured to connect to one of a forearm portion and an upper arm portion and a housing structure configured to connect to the other of the forearm portion and the upper arm portion.

In one embodiment, the fixed member structure is connected to the forearm portion and the housing structure is connected to the upper arm portion. In another embodiment, the fixed member structure is connected to the upper arm portion and the housing structure is connected to the forearm portion. The housing structure is rotatable relative to the fixed member structure about an axis of rotation of the forearm portion.

The powered gearbox mechanism is disposed within and supported by the housing structure. In one embodiment, the powered gearbox mechanism may include a motor connected to the housing structure, a planetary frictional drive connected to a motor shaft of the motor, and a strain wave gear set having an input driven by the frictional drive and an output attached to the fixed member structure. The powered gearbox mechanism is configured to convert an output of the motor into a rotation of the housing structure relative to the fixed member structure, thereby causing the rotation of the forearm portion to varying angular positions relative to the upper arm.

The planetary frictional drive includes a sun element connected to the motor shaft, a ring element fixed to the housing structure, and a set of planet elements for driving the input of the strain wave gear set. The input of the strain wave gear set may be a wave generator. The output of the strain wave gear may be a flex spline. The strain wave gear set includes a circular spline connected to the housing structure.

In another embodiment, the powered gearbox mechanism further includes a brake mechanism disposed between the planetary frictional drive and the strain wave gear set. An input of the brake mechanism is coupled to and driven by the set of planet elements of the planetary frictional drive, and an output of the brake mechanism is coupled to and drives the input of the strain wave gear set.

The powered gearbox mechanism may further include a gearbox output attached to the output of the strain wave gear set.

The powered gearbox mechanism may further include a gearbox hub attached to the gearbox output and the fixed member structure.

The planetary frictional drive and the strain wave gear set share a common longitudinal axis. The strain wave gear set is arranged downstream of the frictional planetary drive along the shared axis.

DETAILED DESCRIPTION OF THE INVENTION

The powered gearbox mechanism disclosed herein is a motor driven mechanism to rotate the mass of a lever arm to varying angular positions. According to an embodiment of the present invention, the moment force of the lever arm is balanced by an opposite moment force applied by the powered gearbox mechanism.

Figure 1:
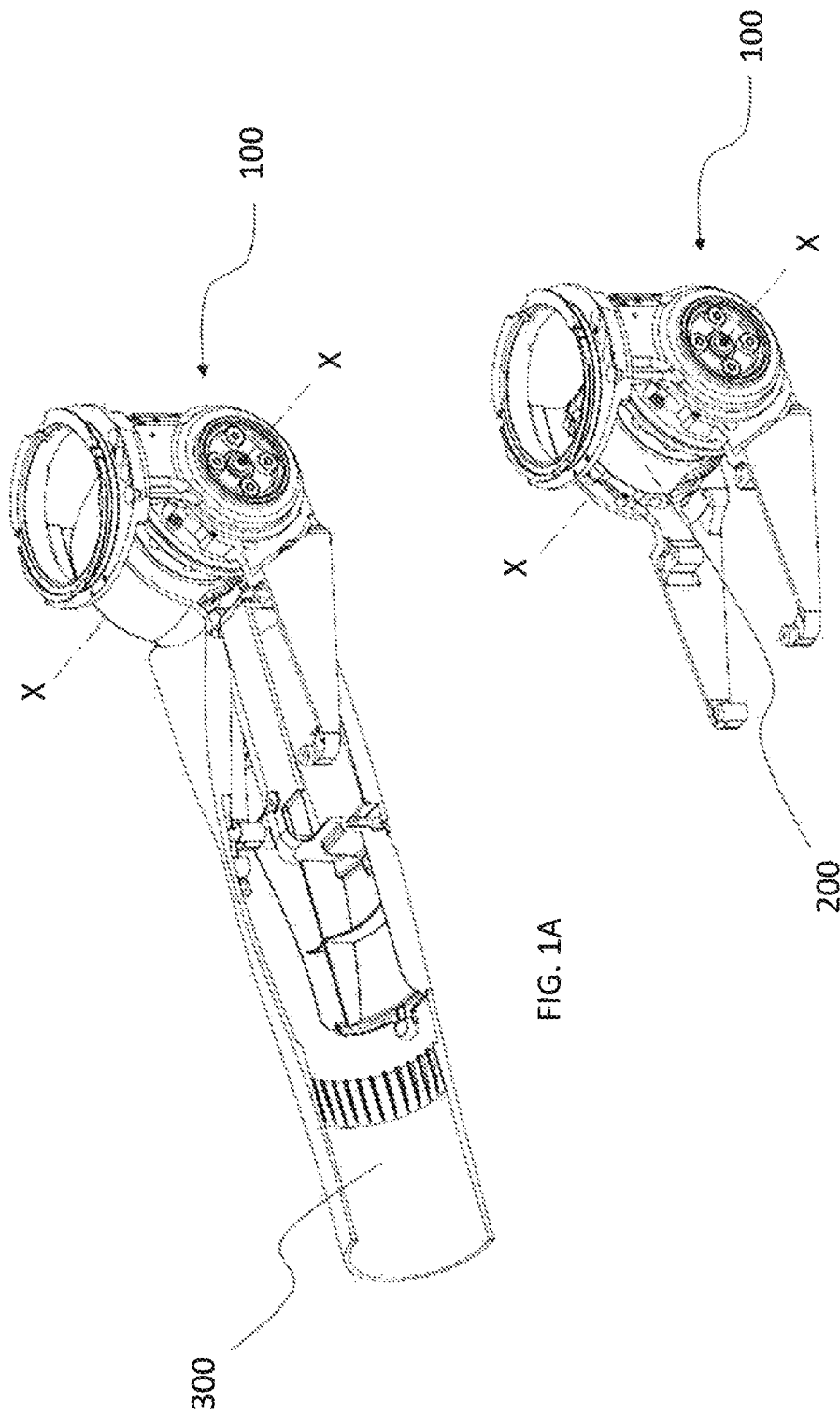
FIG. 1A is a perspective view showing a prosthetic elbow attached to a lever arm member having a powered gearbox mechanism in accordance with an embodiment of the present invention.
FIG. 1B is a perspective view showing a standing-alone prosthetic elbow having a powered gearbox mechanism in accordance with an embodiment of the present invention.

FIGS. 1A and 1B illustrate a prosthetic elbow joint 100 including a powered gearbox mechanism 200. The elbow joint may be connected to a lower portion and an upper portion. The elbow joint is a pivot joint between the upper portion and lower portion. The upper portion may be referred to as an upper arm portion as it connects to a user's upper arm or upper arm prosthetic (not shown in FIG. 1). The lower portion may be referred to as a lever arm member or a forearm portion 300. The forearm portion 300 may rotate about an axis x-x of the elbow joint relative to the upper arm portion when the forearm bends or extends.

Without a powered gearbox mechanism, under the influence of the gravity, the weight of the lever arm member 300 will pull the lever arm member itself down so that the prosthetic elbow will not be able to hold the lever arm member up. By utilizing a powered gearbox mechanism, the user of the prosthetic elbow will be able to hold up the forearm portion so that the forearm portion does not always fall downward under its own weight. The gearbox mechanism can also move the forearm up and down since it is powered by a motor.

Figure 2:
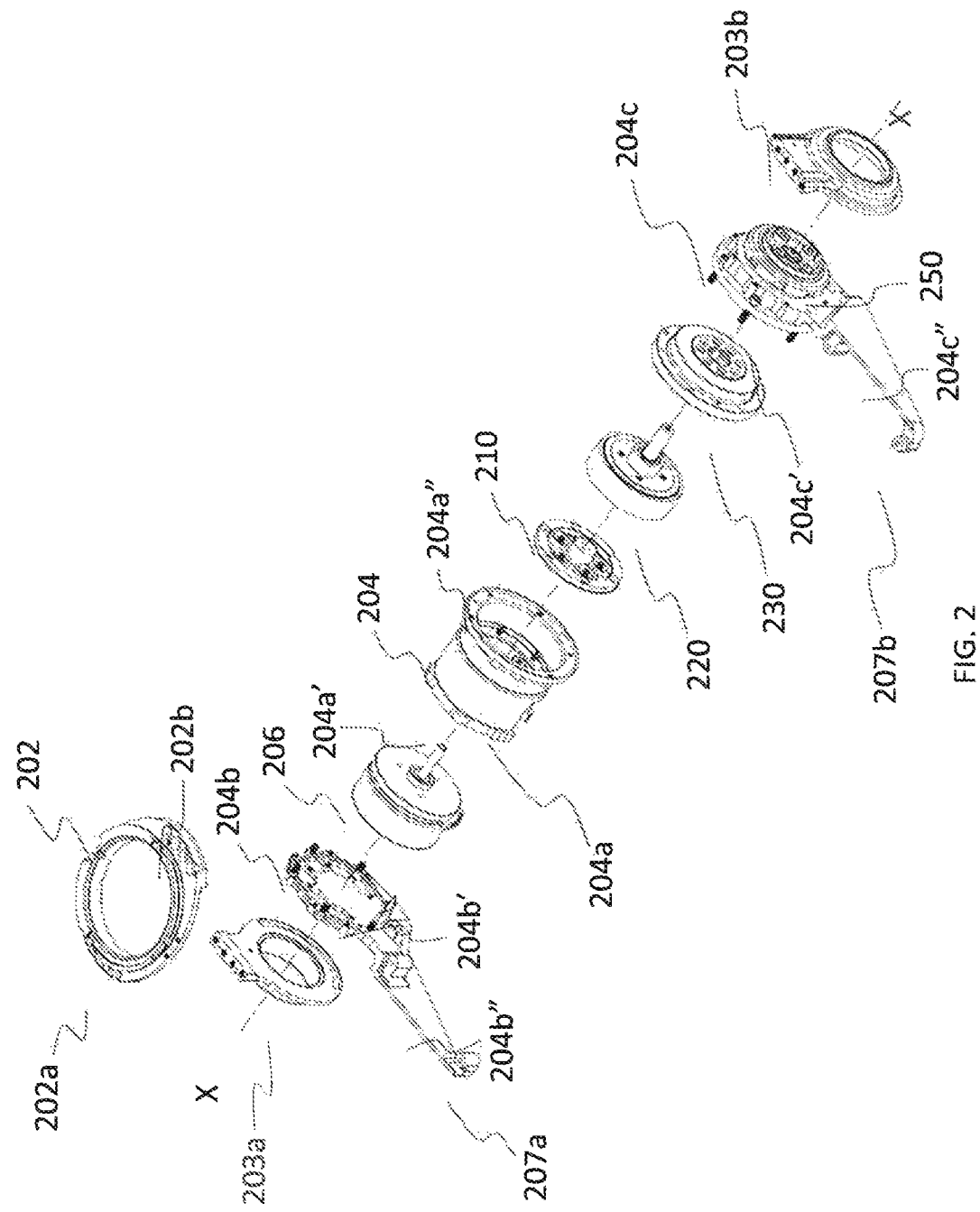
FIG. 2 is a perspective exploded view showing an prosthetic elbow having a powered gearbox mechanism in accordance with an embodiment of the present invention.

FIG. 2 illustrates an exploded view of a prosthetic elbow 100 showing the components of a powered gearbox mechanism in accordance with an embodiment of the present invention.

In this embodiment, the prosthetic elbow joint 100 includes fixed members 202, 203a and 203b. The fixed member 202 is a socket configured to be connected to an upper arm portion (not shown). A pair of substantially parallel fixed members 203a, 203b are connected to two sides 202a, 202b of the fixed member 202 by fasteners such as screws and both are perpendicular to the fixed member 202. The fixed member 202 and the pair of the fixed members 203a, 203b are mounted together forming a fixed structure for containing and supporting the powered gearbox mechanism 200.

The elbow joint 100 includes a housing structure 204 for supporting the powered gearbox mechanism 200. The housing structure has a housing structure member 204a and two housing structure side members 204b, 204c. The housing structure member 204a is disposed about an axis x-x. The housing structure member 204a is generally cylindrical and extends between the housing structure side members 204b, 204c. The two housing structure side members 204b, 204c are substantially parallel to each other and extend outwardly perpendicular to the axis x-x. The housing structure side members 204b, 204c each have a circular portion 204b', 204c' extending to an elongated arm portion 204b", 204c". The circular portions 204b', 204c' each are mounted to one of the two sides 204a', 204a" of the cylindrical housing structure member 204a by fasteners such as screws. When the circular portions 204b', 204c' of the housing structure side members 204b, 204c are attached to the cylindrical housing structure member 204a, the housing structure side members 204b, 204c and the cylindrical housing structure member 204a form a housing structure 204 capable of rotating about the axis x-x within the fixed member structure formed by the fixed member 202, and the pair of the fixed members 203a, 203b. The elongated arm portions 204b", 204c" may be configured to be attached to the forearm portion 300 at the ends 207a, 207b of the elongated arm portions 204b", 204c" such that when the forearm portion bends or extends relative to the upper arm portion about the elbow joint axis x-x, the housing structure 204 rotates about the axis x-x with the forearm portion. In an alternative embodiment, the fixed member structure is attached to the forearm portion and the housing structure is attached to the upper arm portion. For example, the elongated arm portions 204b", 204c" of the housing structure 204 may be configured to be attached to the upper arm portion at the ends 207a, 207b of the elongated arm portions 204b", 204c".

In one embodiment, the powered gearbox mechanism 200 includes a motor 206, a planetary frictional drive set 210, and a strain wave gear set 230. In another embodiment, the powered gearbox mechanism 200 may further include a brake mechanism 220 to prevent the gearbox mechanism being back-driven. FIGS. 3-7 and 9-10 show examples of how each component of the powered gearbox mechanism 200 may be disposed within the housing structure and how various components of the powered gearbox mechanism 200 may be configured and connected relative to one another.

Figure 3:
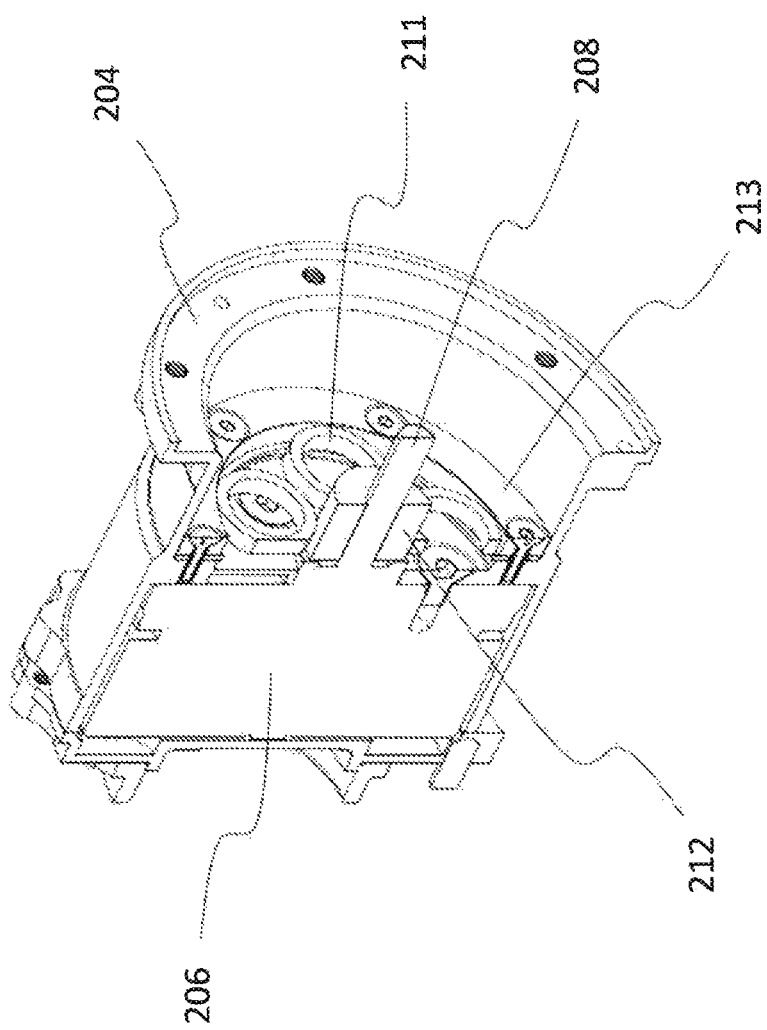
FIG. 3 is a perspective cross sectional view showing a part of the powered gearbox mechanism in accordance with an embodiment of the present invention.
Figure 4:
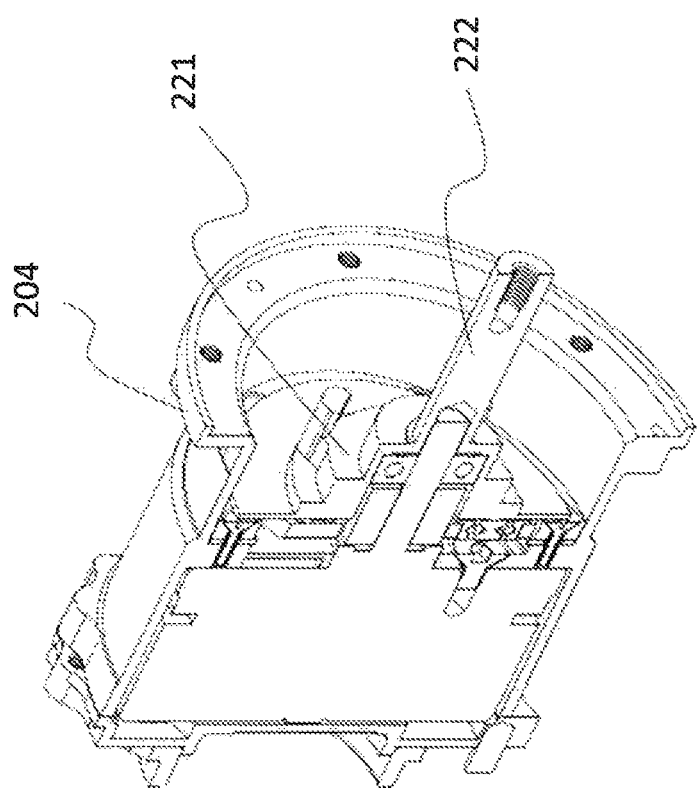
FIG. 4 is another perspective cross sectional view showing a part of the powered gearbox mechanism in accordance with an embodiment of the present invention.
Figure 5B:
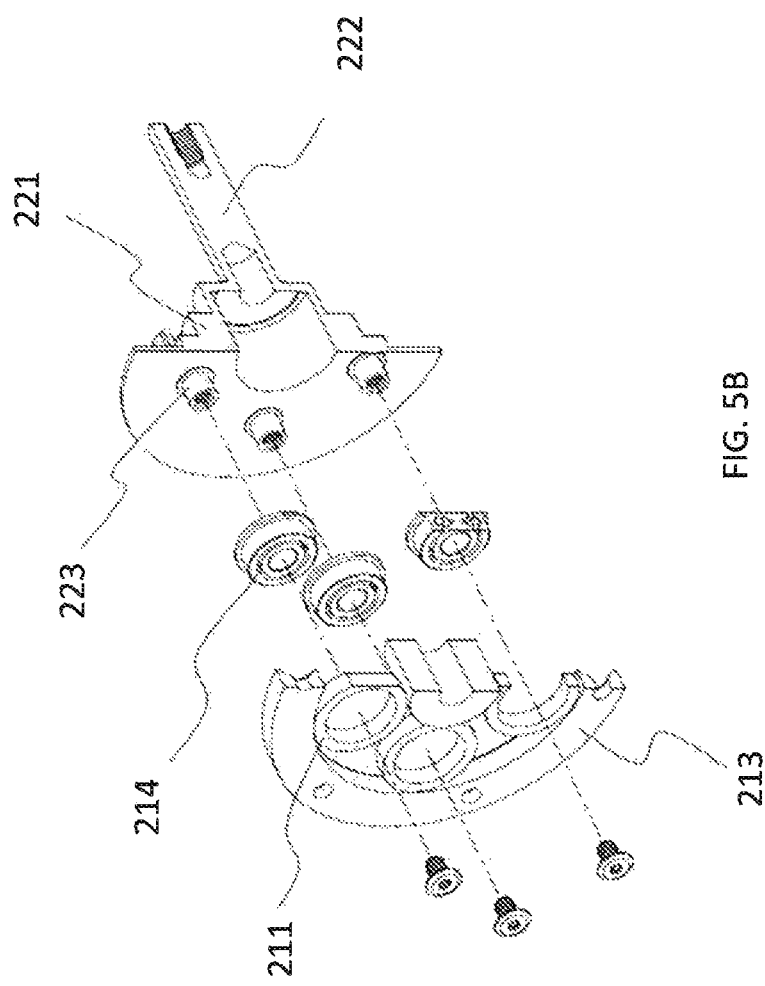
FIG. 5B is an exploded view of FIG. 5A.
Figure 5A:
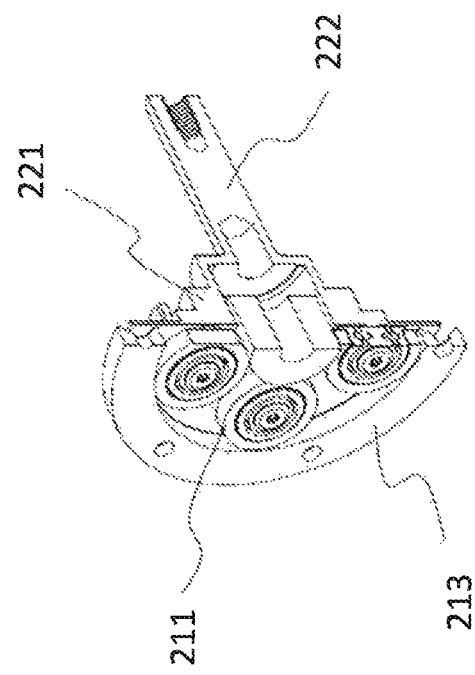
FIG. 5A is another perspective cross sectional view showing a part of the powered gearbox mechanism in accordance with an embodiment of the present invention.

As shown in FIG. 3, the motor 206 is attached to the housing structure 204. The planetary frictional drive set 210 includes a ring element 213, a sun element 212 and a plurality of planet elements 211. The planet elements 211 of the planetary frictional drive set 210 are rollers having a frictional contact with the sun element 212. The sun element 212 is mounted on the shaft 208 of the motor 206. As shown in FIG. 3, the ring element 213 of the planetary frictional drive 210 is fixed to the housing structure 204. FIGS. 4 and 5A-5B show the input element 221 of the brake mechanism. The input element 221 has a shaft 222. As shown in FIG. 5B, the planet elements 211 are attached by bearings 214 on posts 223 on the input element 221 of the brake mechanism. Rotation of the sun element 212 causes the planet elements 211 to orbit around the sun element 212 within the ring element 213 and drives the rotation of the brake input element 221.

Figure 6:
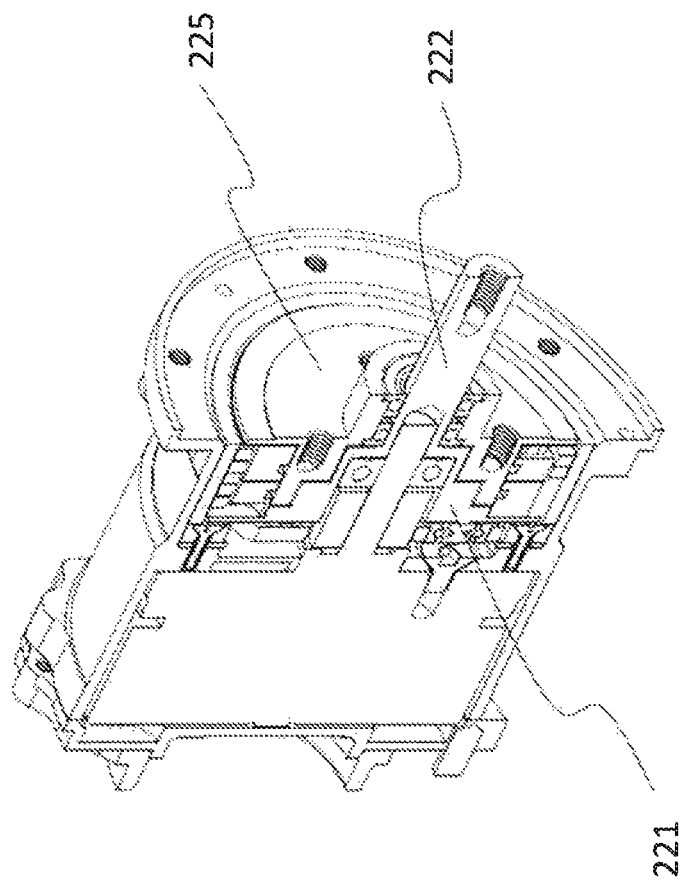
FIG. 6 is another perspective cross sectional view showing a part of the powered gearbox mechanism in accordance with an embodiment of the present invention.
Figure 7:
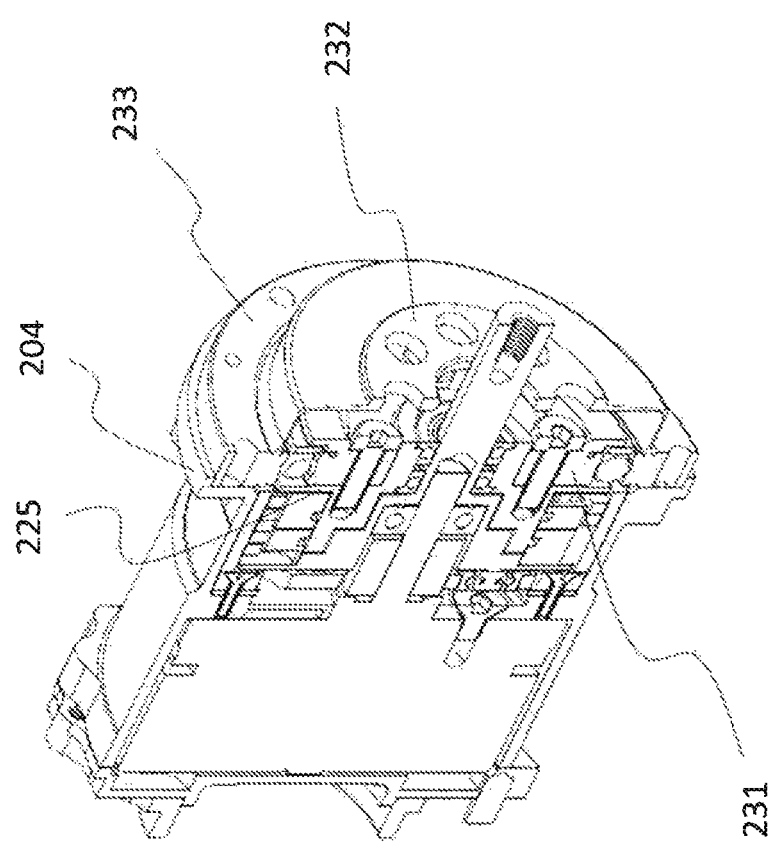
FIG. 7 is another perspective cross sectional view showing a part of the powered gearbox mechanism in accordance with an embodiment of the present invention.
Figure 8:
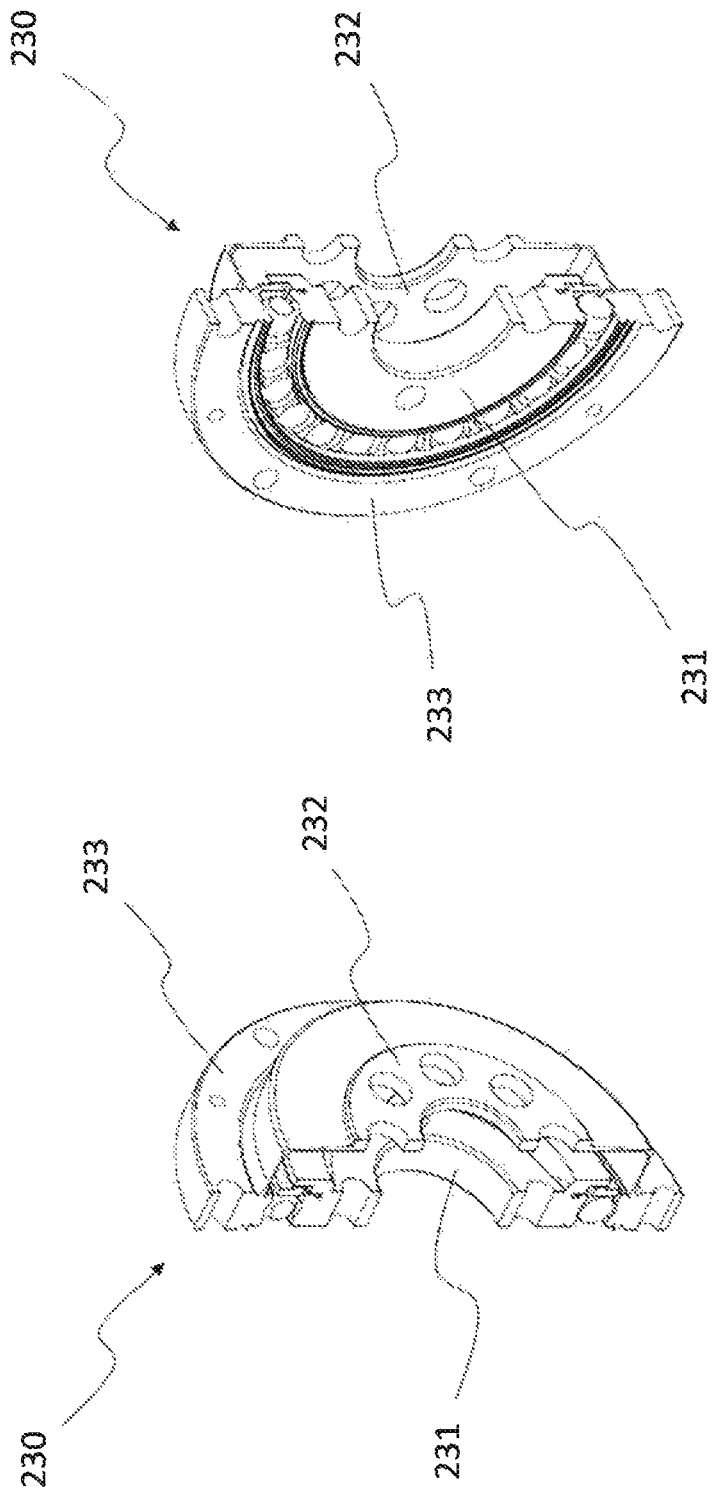
FIG. 8A is a perspective cross sectional view showing a strain wave gear set in accordance with an embodiment of the present invention.
FIG. 8B is another perspective cross sectional view showing a strain wave gear set in accordance with an embodiment of the present invention.

The brake input element 221 drives the brake output element 225, as shown in FIG. 6. The brake output element 225 is supported on bearings on shaft 222 of the brake input element 221. The brake output element 225 is fastened to and drives the input of the strain wave gear set 230, as shown in FIG. 7. FIGS. 8A and 8B show a cut-away view of the strain wave gear set 230 including the wave generator 231, a flex spline 232 and a circular spline 233. The wave generator 231 is the input of the strain wave gear set 230. The flex spline 232 is the output of the strain wave gear set 230. The circular spline 233 of the strain wave gear set 230 is fixed to the housing structure 204. The strain wave gear set 230, including the wave generator 231, a flex spline 232 and a circular spline 233, is disposed downstream of the planetary frictional drive 210. As shown in FIG. 7, the strain wave gear set 230 and the planetary frictional drive 210 do not have any overlap along the x-x axis.

Figure 9:
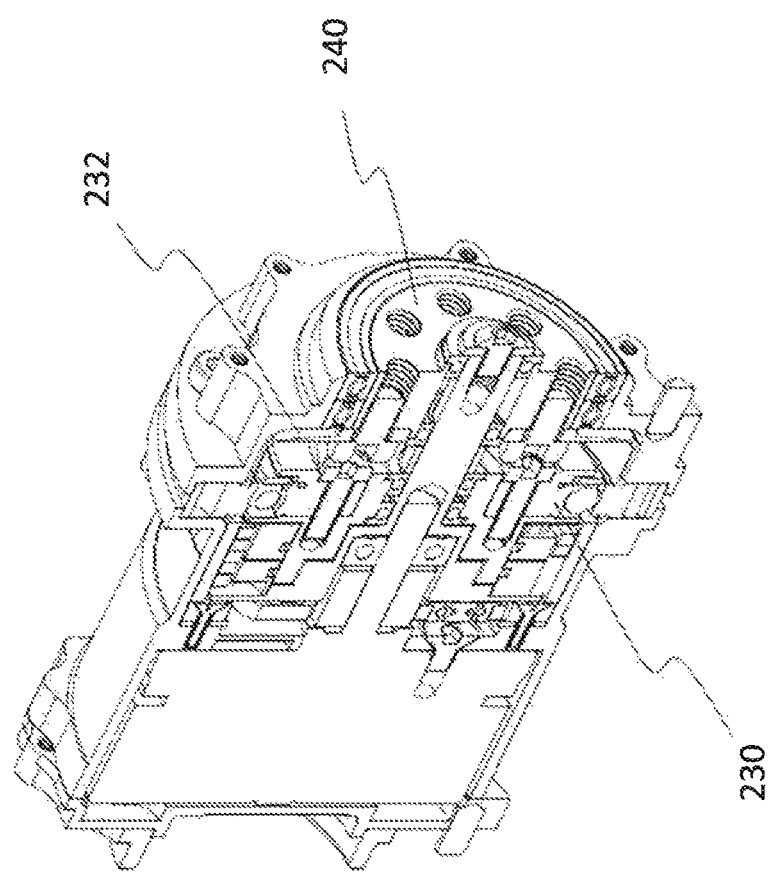
FIG. 9 is another perspective cross sectional view showing a part of the powered gearbox mechanism in accordance with an embodiment of the present invention.
Figure 10:
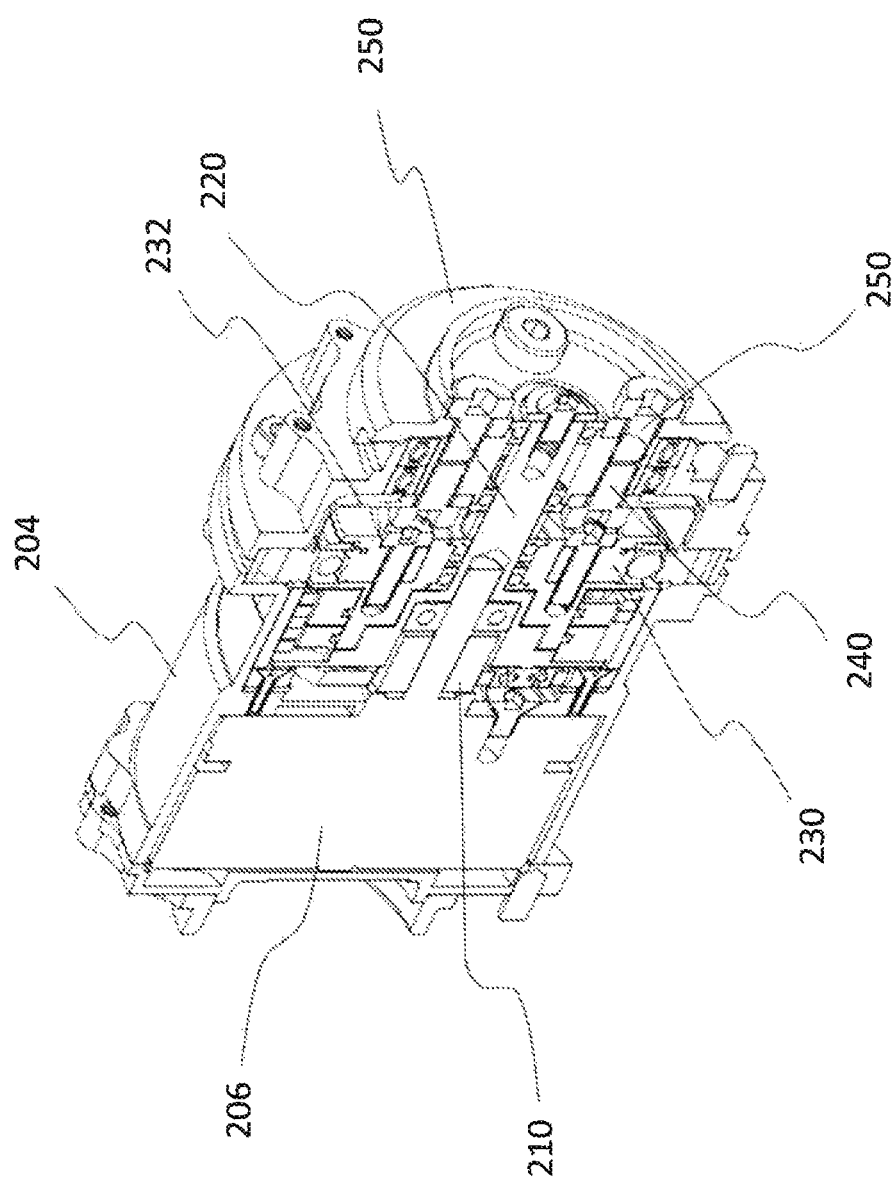
FIG. 10 is another perspective cross sectional view showing a part of the powered gearbox mechanism in accordance with an embodiment of the present invention.

The flex spline 232 is attached to an output 240 of the powered gearbox mechanism, as shown in FIG. 9. The gearbox output 240 is further attached to a gearbox hub 250. As shown in FIG. 10, the gearbox output 240 and the gearbox hub 250 are used to accommodate the assembly of the housing structure and the gearbox mechanism to the fixed member structure. The gearbox output 240 and the gearbox hub 250 may be integrated into one single piece. The flex spline 232, the gearbox output 240 and the gearbox hub 250 are connected together and do not move independent of one another, as shown in FIG. 10. The assembly of the flex spline 232, the gearbox output 240 and the gearbox hub 250 is fixed to the fixed member structure 203b and do not move relative to the fixed member structure 203b.

FIG. 10 is a cut-away view showing all the components of a powered gearbox in accordance with an embodiment of the present invention, including the motor 206, the planetary frictional drive 210, the brake mechanism 220, the strain wave gear set 230, the gearbox output 240, and the hub 250. Driven by the motor 206, the sun element 212 of the planetary frictional drive 210 causes the planet elements 211 of the planetary frictional drive 210 to rotate around the axis x-x. The rotation of the planet elements 211 is subsequently transferred to the input, i.e., the wave generator 231, of the strain wave gear set 230, such that the output, i.e., the flex spline 232, of the strain wave gear set 230 will move relative to the circular spline 233. Since the flex spline 232, the gearbox output 240 and the gearbox hub 250 are all bolted together and fixed to the fixed member structure, it is the circular spline 233 that ends up rotating relative to the fixed member structure. Since the circular spline is connected to the housing structure 204, the rotation of the circular spline 233 will then cause the housing structure 204 to rotate relative to the fixed member structure. As a result, the forearm will rotate relative to the upper arm driven by the motor 206.

The brake mechanism may be optional in other embodiments.

According to this embodiment, the strain wave gear set 230 is arranged downstream of the frictional planetary drive 210. The planetary frictional drive 210 and the strain wave gear set 230 share a common longitudinal axis x-x. The motor 206, the planetary frictional drive 210, the brake mechanism 220, the strain wave gear set 230, the gearbox output 240 and the gearbox hub 250 are all symmetrically disposed about the elbow axis x-x.

One of the advantages of the gearbox mechanism according to the embodiment of the present invention is a low noise level. With the combination of the frictional planetary drive and the strain wave gear set, the revolutions of the electrical motor are converted into a much slower, more steady and quieter rotation of the housing structure relative to the fixed member structure as the forearm rotates about the elbow joint relative to the upper arm portion.

In the application of an upper limb above-elbow prosthetic device, the gearbox mechanism is coaxially located at the axis of rotation of the elbow joint locating the majority of its mass at the axis of rotation of the elbow joint therefore allowing the center of mass of the prosthetic device to be located more proximal. By locating the center of mass of the prosthetic as proximal as possible, the prosthetic device places less of a moment force on the residual limb, resulting in the prosthetic typically feeling more comfortable to the end user and being perceivably lighter than having a more distal mass. The use of a friction roller planetary set produces less noise than a similar geared planetary set reducing the overall noise generated by the gearbox.

As will be clear to those of skill in the art, the embodiments of the present invention illustrated and discussed herein may be altered in various ways without departing from the scope or teaching of the present invention. Also, elements and aspects of one embodiment may be combined with elements and aspects of another embodiment. It is the following claims, including all equivalents, which define the scope of the invention.

The invention claimed is:

1. A prosthetic elbow with a powered gearbox mechanism, comprising:
   a fixed member structure configured to connect to one of a forearm portion and an upper arm portion;
   a housing structure configured to connect to the other of the forearm portion and the upper arm portion, the housing structure rotatable relative to the fixed member structure about an axis of rotation of the forearm portion; and
   a powered gearbox mechanism for rotating the forearm portion to varying angular positions about an elbow axis, the powered gearbox mechanism disposed within and supported by the housing structure, the powered gearbox mechanism comprising:
      a motor connected to the housing structure and having a motor shaft,
      a planetary frictional drive connected to the motor shaft and the housing structure, and
      a strain wave gear set having an input driven by the planetary frictional drive and an output attached to the fixed member structure; and
   a brake mechanism,
   wherein the planetary frictional drive includes a sun element connected to the motor shaft, a ring element fixed to the housing structure, and a set of planet elements for driving the input of the strain wave gear set,
   wherein an input of the brake mechanism is coupled to and driven by the set of planet elements of the planetary frictional drive, and an output of the brake mechanism is coupled to and drives the input of the strain wave gear set, and
   wherein the powered gearbox mechanism is configured to convert an output of the motor into a rotation of the housing structure relative to the fixed member structure, thereby causing the rotation of the forearm portion to varying angular positions relative to the upper arm.

2. The prosthetic elbow with a powered gearbox mechanism according to claim 1, wherein the input of the strain wave gear set is a wave generator.

3. The prosthetic elbow with a powered gearbox mechanism according to claim 1, wherein the output of the strain wave gear set is a flex spline.

4. The prosthetic elbow with a powered gearbox mechanism according to claim 1, wherein the strain wave gear set includes a circular spline connected to the housing structure.

5. The prosthetic elbow with a powered gearbox mechanism according to claim 1, wherein the powered gearbox mechanism further comprises a gearbox output attached to the output of the strain wave gear set and a gearbox hub attached to the gearbox output and the fixed member structure for accommodating the housing structure and the gearbox mechanism.

6. The prosthetic elbow with a powered gearbox mechanism according to claim 5, wherein the gearbox hub and the gearbox output are one piece.

7. The prosthetic elbow with a powered gearbox mechanism according to claim 1, wherein the planetary frictional drive and the strain wave gear set share a common longitudinal axis, the strain wave gear set is arranged downstream of the frictional planetary drive along the axis.

* * * * *